United States Patent
DeGrandpre

(10) Patent No.: US 7,026,165 B2
(45) Date of Patent: Apr. 11, 2006

(54) CALIBRATION-FREE OPTICAL CHEMICAL SENSORS

(75) Inventor: Michael D. DeGrandpre, Missoula, MT (US)

(73) Assignee: The University of Montana, Missoula, MT (US)

( * ) Notice: Subject to any disclaimer, the term of this patent is extended or adjusted under 35 U.S.C. 154(b) by 603 days.

(21) Appl. No.: 09/775,386

(22) Filed: Jan. 31, 2001

(65) Prior Publication Data

US 2002/0001851 A1 Jan. 3, 2002

Related U.S. Application Data

(60) Provisional application No. 60/178,966, filed on Jan. 31, 2000.

(51) Int. Cl.
*G01N 21/75* (2006.01)

(52) U.S. Cl. ................. 436/164; 436/127; 436/133; 436/172

(58) Field of Classification Search ............... 422/50, 422/55, 58, 82.05, 82.08, 82.09, 82.13; 436/164, 436/172, 127, 133
See application file for complete search history.

(56) References Cited

U.S. PATENT DOCUMENTS 5,116,759 A * 5/1992 Klainer et al. ............ 435/287.2
5,434,084 A * 7/1995 Burgess, Jr. ................. 436/52

OTHER PUBLICATIONS

MacCraith, B.D.; McDonagh, C.; McEvoy, A.K.; Butler, T.; O'Keefe, G.; Murphy, V.J. *Sol–Gel Sci. Tech.* 1998, 8, 1053–1061.

Spichiger–Keller, U.E. *Chemical Sensors and Biosensors for Medical and Biological Applications*, Wiley–VCH: Weinheim, 1998.

Berman, R.J.; Christian, G.D.; Burgess, L.W. *Anal. Chem.* 1990, 62, 2066–2071.

DeGrandpre, M.D. *anal. Chem.* 1993, 65,331–337.

DeGrandpre, M.D.; Hammar, T.R.; Smith, S.P.; Sayles, F.L. *Iimnol. And Oceanog.* 1995, 40, 969–975.

Byrne, R.H.; Breland, J.A. *Deap–Sea Res.* 1989,36,803–810.

Clayton, T.D.; Byrne, R.H. *Deep–Sea Res.* 1993, 40, 2115–2129.

Goyet, C.; Walt, D.R.; Brewer, P.G. *Deep–Sea Res.* 1992, 39, 1015–1026.

(Continued)

*Primary Examiner*—Jill Warden
*Assistant Examiner*—LaToya I. Cross
(74) *Attorney, Agent, or Firm*—Saliwanchik, Lloyd & Saliwanchik

(57) ABSTRACT

An apparatus and method for taking absorbance-based chemical measurements are described. In a specific embodiment, an indicator-based $pCO_2$ (partial pressure of $CO_2$) sensor displays sensor-to-sensor reproducibility and measurement stability. These qualities are achieved by: 1) renewing the sensing solution, 2) allowing the sensing solution to reach equilibrium with the analyte, and 3) calculating the response from a ratio of the indicator solution absorbances which are determined relative to a blank solution. Careful solution preparation, wavelength calibration, and stray light rejection also contribute to this calibration-free system. Three $pCO_2$ sensors were calibrated and each had response curves which were essentially identical within the uncertainty of the calibration. Long-term laboratory and field studies showed the response had no drift over extended periods (months). The theoretical response, determined from thermodynamic characterization of the indicator solution, also predicted the observed calibration-free performance.

8 Claims, 8 Drawing Sheets

OTHER PUBLICATIONS

Goswami, K.; Kennedy, J.A.; Dandge, D.K.; Klainer, S.M.; Tokar, J.M. *Proc. SPIE—Int. Soc. Opt. Eng.* 1990, 1172, 225–232.
Lefevre, N.; Ciabrini, J.P.; Michard, G.; Brient, B.; DuChaffaut, M.; Merlivat, L. *Mar. Chem.* 1993, 42, 189–198.
Weeks, D.A.; Johnson, K.S. *Anal. Chem.* 1996, 68, 2717–2719.
Peterson, J.L.; Goldstein, S.R.; Fitzgerald, R.V.; Buckhold, K.K. *Anal. Chem.* 1980, 52, 864–869.
Zhou, Q.; Kritz, D.; Bonnell, L.; Sigel, G. *App. Opt.* 1989, 28, 2022–2025.
Chau, L.K.; Porter, M.D. *Anal. Chem.* 1990, 62, 1964–1971.
DeGrandpre, M.D., *Anal. Chem.* 1999, 71, 1152–1159.
Ingle, J.D.; Crouch, S.R. *Spectrochemical Analysis.* Prentice–Hall: New Jersey, 1998.
Thompson, R.B.; Jones, E.R. *Anal. Chem.* 1993, 65, 730–734.
McDonagh, C.; MacCraith, B.D.; Mc envoy, A.K. *Anal. Chem.* 1998, 70, 45–50.
Wolfbeis, O.S.; Posch, H.E.; Kroneis, H.W. *Anal. Chem.* 1985, 57, 2556–2561.
Klimant, I.; Meyer, V.; Kuhl, M. *Linmol. Oceanog.* 1995, 40, 1159–1165.
Draxler, S.; Lippitsch, M.E. *Proc. SPIE–13 Int. Soc. Opt. Eng.* 1993, 2085, 61–67.
Tabacco, M.B.; Uttamial, M.; McAllister, M.; Walt, D.R. *Anal. Chem.* 1999, 71, 154–161.
Burgess, L. W. *Sensors and Actuators B 29* 1995, 10–15.
Weigl, B.H.; Holobar, A. *Analytica Chimica Acta* 282, 1993, 335–343.
Wolfbeis, O.S.; Weis, L. J. *Anal. Chem.* 1988, 2028–2030.
Luo, S.; Walt, D.R. *Anal. Chem.* 1989, 61, 174–177.
Walt, D.R.; Gabor, G.; Goyet, C. *Analytica Chimica Acta* 274, 1993, 47–52.
DeGrandpre, M.D.; Hammar, T.R.; Wallace, D.W.R.; Wirick, C.D. *Limnol. Oceanogr.* 42(1) 1997, 21–28.

\* cited by examiner

US 7,026,165 B2

CALIBRATION-FREE OPTICAL CHEMICAL SENSORS

This provisional application claims benefit of Ser. No. 60/178,966 filed Jan. 31, 2000. +gi The subject invention was made with government support under a research project supported by the Department of Energy Ocean Margins Program Grant No. DOE-DEFG03-94ER6224. The government has certain rights in this invention.

BACKGROUND OF THE INVENTION

Research on optical chemical sensors blossomed over the past 15–20 years as a result of the availability of novel and inexpensive waveguides and the ever-increasing need for sensors for a wide range of chemical applications. Most chemical sensors however require calibration since sensor response is not consistent between sensors nor is it stable over time.

Reagent-based Optical Chemical Sensors (hereafter referred to as ROCS) generated substantial excitement early on in their development because they promised improved performance and versatility over their electrochemical sensor analogs. These potential advantages included greater stability and selectivity and a simple, characterizable response. But, after nearly 20 years of research and development, these advantages have yet to be fullly realized[1,2].

The majority of ROCS use fiber optics to direct light into a small membrane-enclosed volume, resulting in single-ended electrode-like probes[3]. In most ROCS designs, a calorimetric or fluorimetric reagent is entrapped within the membrane at the fiber tips. The membrane serves a variety of important purposes- it contains and protects the analyte-selective reagent, it provides an additional level of selectivity for groups of different compounds (e.g. gases, hydrophilic or hydrophobic species), and it acts as a diffuse reflector of the light transmitted through, or emitted from, the selective reagent. Chemical sensing is generally accomplished by simply monitoring the change in light intensity in the presence of the analyte of interest. Light intensity changes unrelated to the analyte such as light source fluctuations or changes in the fiber optic transmission are compensated for by using a reference light intensity at a wavelength insensitive to the analyte concentration. Even so, these ROCS designs have significant stability problems that primarily originate from the changes in the composition of the entrapped reagent chemistry[1]. To improve ROCS performance, researchers began investigating methods for renewing the reagent[4,5].

Although steps have been taken in achieve consistency and stability among optical chemical sensors, a calibration-free sensor displaying long-term stability and an identical response from sensor to sensor has not yet been described. A need therefore exists for such a calibration-free sensor that can be applied to a wide range of biomedical, industrial and environmental applications.

All patents, patent applications, provisional patent applications and publications referred to or cited herein, or from which a claim for benefit of priority has been made, are incorporated by reference in their entity to the extent they are not inconsistent with the explicit teachings of the specification.

BRIEF SUMMARY OF THE INVENTION

The subject invention involves an apparatus for taking absorbance-based chemical measurements which requires no calibration. The subject apparatus comprises a reagent-based optical chemical sensor/analyzer having an analyte-selective reagent which transduces analyte concentration into an optical signal, the apparatus also comprises a means for renewing the reagent, a means for allowing the reagent to reach equilibrium with the analyte and, means for calculating response from a ratio of reagent solution absorbance which is determined relative to a blank solution. This calibration-free system displays a response which is consistent among sensors/analyzers and shows no drift over time. Methods of taking absorbance-based chemical measurements using the calibration-free apparatus of the subject invention are also described.

DETAILED DESCRIPTION OF THE INVENTION

The subject invention involves a device for taking absorbance-based chemical measurements. The subject device is calibration-free displaying a consistent response between sensors/analyzers and showing no drift over time.

Reagent-based optical chemical sensors (ROCS) utilize an analyte-selective reagent to transduce analyte concentration into an optical signal. Light is used to generate and quantify the optical signal. Thus, changes in analyte concentration within the system are detected by monitoring the change in light intensity of the analyte-selective reagent in the presence of the analyte. To achieve a calibration-free reagent-based optical chemical sensor a typical sensor must be run under the following conditions: a) the analyte-selective reagent, or sensing solution, is renewable, b) the analyte-selective reagent is allowed to reach equilibrium with the analyte and, c) the sensor response is calculated from a ratio of the reagent absorbances which are determined relative to a blank solution.

Sensors/analyzers suitable for use in the subject invention include any device whose analytical reaction is based upon the creation of two light absorbing forms of a selective reagent which absorb light at different wavelengths. As used herein, sensors are reagent-based optical chemical devices used in situ, analyzers do not operate in situ but receive samples to be analyzed independently.

Figure 1:
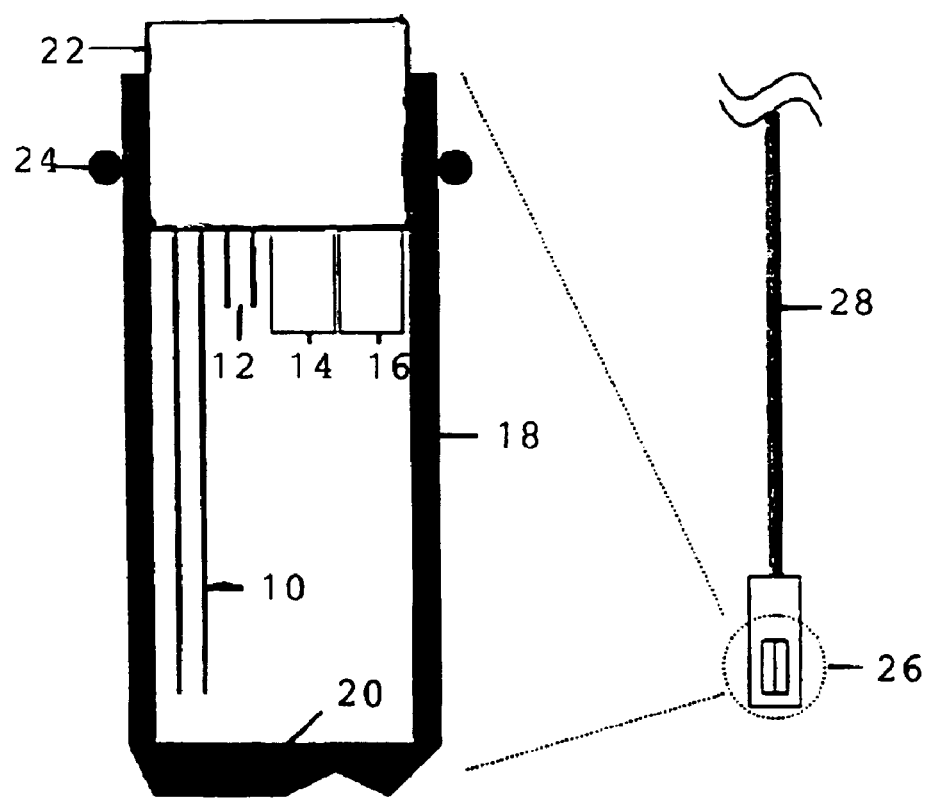
FIG. 1 shows a single-ended renewable-reagent $pCO_2$ sensor design. Note: individual components are not drawn to scale.
Figure 2:
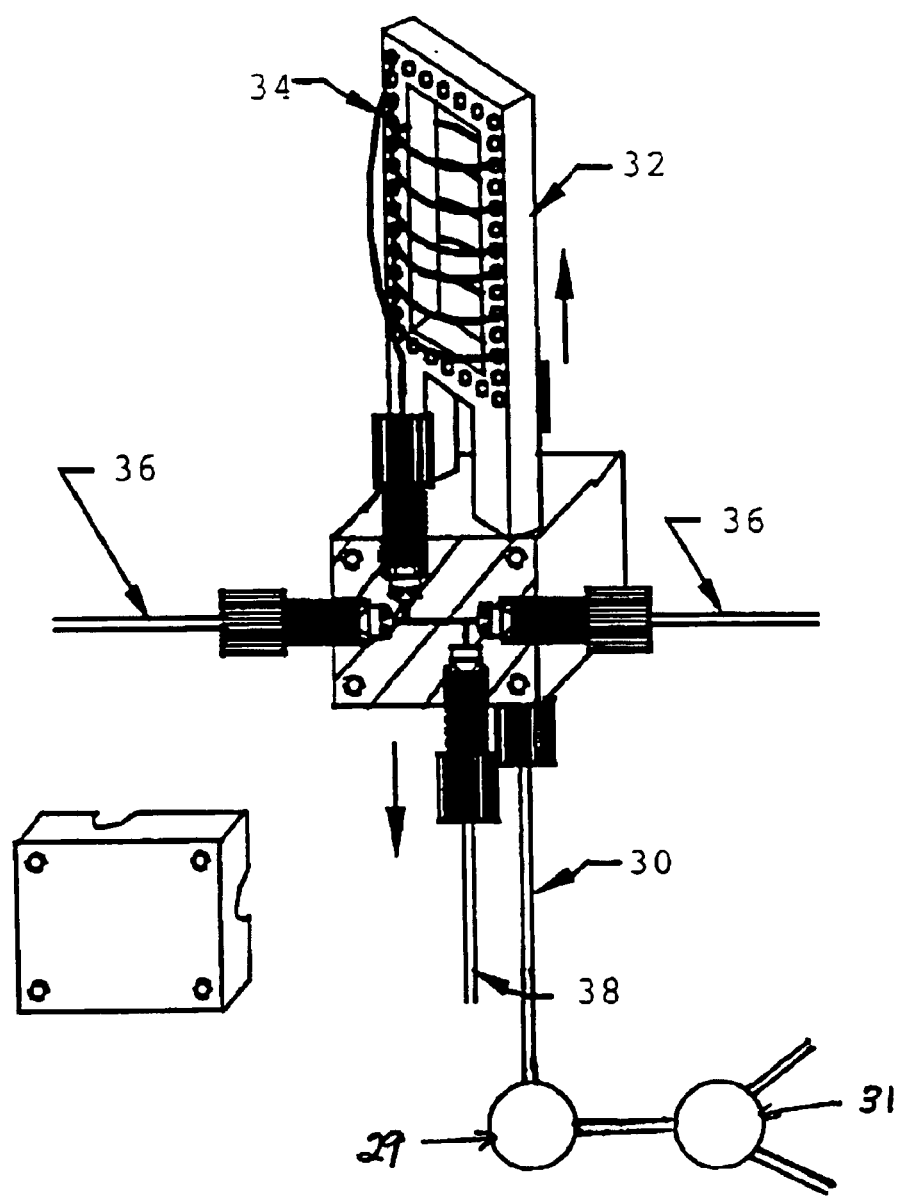
FIG. 2 shows a cut away view of a Submersible Autonomous Moored Instrument for $CO_2$ (SAMI-$CO_2$) sensor design based on a membrane-equilibrator and fiber optic flow cell.

In an exemplified embodiment of the calibration-free device of the subject invention a Submersible Autonomous Moored Instrument for $CO_2$ (SAMI-$CO_2$) is used as the sensor. The SAMI-$CO_2$ design was based upon previous $CO_2$ sensor designs which used a colorimetric pH indicator entrapped within a gas permeable membrane[6]. However, unlike previous sensors, the reagent is renewed during each measurement cycle. The original single-ended probe design is shown in FIG. 1[7,8]. Briefly, the sensor comprises a reagent delivery capillary tube 10, a reagent exit capillary tube 12, fiber optic from source 14, fiber optic to detection system 16, white silicone rubber membrane 18, white silicone sealant 20, epoxy sealant 22, an o-ring 24, a sensor stainless steel housing 26, and a fiber optic and capillary tubing cable 28. The sensor outer diameter ~1 mm. The sensor was subsequently redesigned, finally evolving into a transmission geometry (FIG. 2). The SAMI-$CO_2$ sensor is comprised of a membrane equilibrator attached to a fiber optic flow cell (FIG. 2) (the sensor dimensions and other specifications have been reported previously)[9]. Briefly, the sensor in FIG. 2 comprises a reagent inlet 30, an equilibrator support 32, a silicone membrane equilibrator 34, a fiber optic cable 36 and a reagent outlet 38.

In operation, ambient $CO_2$, or analyte, diffuses through a tubular silicone rubber membrane into a sulfonephthalein (bromothymol blue (BTB)) indicator solution or analyte-selective reagent. The diffusion of $CO_2$ into the indicator solution leads to the formation of carbonic acid which changes the solution pH thereby establishing the equilibrium concentrations of the acid ($HL^-$) and the base ($L^{2-}$) forms of the indicator:

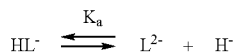

The acid form of the solution absorbs light at 434 nm. The base form of the solution absorbs light at 620 nm. The fully protonated form of the diprotic sulfonephthalein indicator ($H_2L$, pKa=2) is not present in significant amounts at the indicator solution pH (around pH 7).

To achieve the subject calibration-free system, the analyte-selective reagent of the optical chemical sensor/analyzer must be renewable. A variety of pumps 29 and valves 31 are available for supplying new reagent to a sensor/analyzer. A solenoid pump and valve are used in a preferred embodiment. Additionally, peristaltic pumps, syringe pumps, positive displacement pumps, and valves, such as, pinch valves can be used for this purpose.

In the calibration-free system of the subject invention, the analyte-selective reagent must be allowed to reach equilibrium with the analyte (e.g. see previous reaction). This is accomplished by allowing the reagent and analyte suitable time to reach equilibrium. Therefore, a pumping system designed to move reagent through the system must be calibrated to allow adequate time for the indicator solution and analyte to equilibrate.

For example, in an exemplified embodiment in which a SAMI-$CO_2$ is the sensor, indicator solution stored in an isolated reagent bag was pumped into the membrane for each measurement. In initial studies using the sensor design in FIG. 1, the indicator solution was pumped at a rate which did not allow full equilibration with the external $CO_2$, resulting in a diffusion-dependent response. Although this approach had excellent $CO_2$ sensitivity, slow or stopped-flow, which achieved equilibrium with the external solution, was less sensitive to diffusion and temperature and resulted in dramatically improved measurement precision [8]. The sensor design in FIG. 2 required about 5 min. to achieve equilibrium between the indicator and external solution[9]. During each measurement cycle a solenoid pump was activated pushing new indicator solution into the membrane and flushing the $CO_2$-equilibrated solution into the fiber optic flow cell[9]. The SAMI solenoid pump delivers ~50 μL of solution per pulse, which was sufficient to flush out the cell and membrane.

Finally, to achieve the calibration-free system of the subject invention, the response must be calculated from a ratio of the absorbance of the analyte-selective reagent at two different wavelengths, the absorbances determined relative to a blank solution.

The sensor response in the subject calibration-free system is calculated from the analyte-sensitive reagent, or indicator absorbances at two different wavelengths. The wavelengths chosen correspond to the molar absorptivity maxima of the two indicator forms, $$A_\lambda = -\log\frac{I_\lambda}{I_{\lambda 0}} \qquad (1)$$

where $A_\lambda$ is the indicator solution absorbance at wavelength $\lambda$, $I_\lambda$ is the intensity transmitted through the reagent and $I_{\lambda 0}$ is the transmitted intensity through a blank solution. The chosen wavelengths correspond to the molar absorptivity maxima of measurements.

Figure 3:
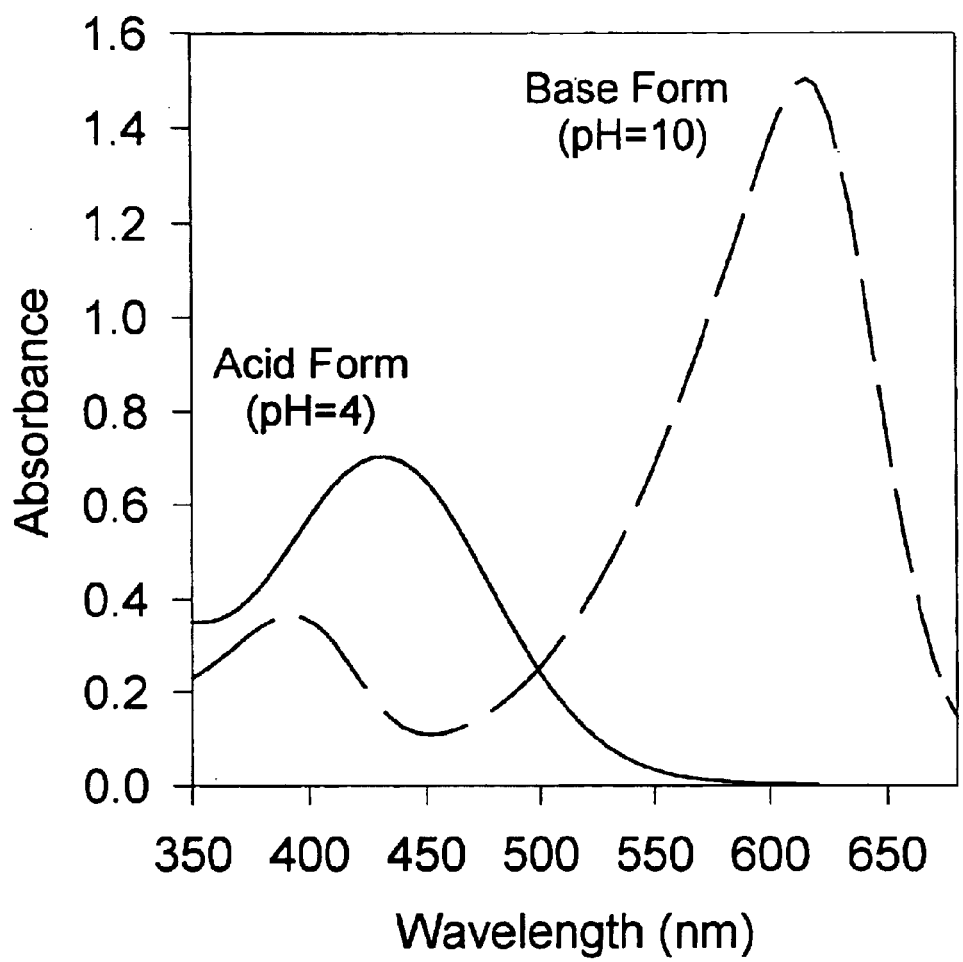
FIG. 3 shows the absorbance spectra of the acid (HL-) and base (L2-) forms of the sulfonephthalien indicator bromothymol blue used in a preferred embodiment of the calibration-free apparatus of the subject invention. The total indicator concentration was ~9.0×10$^{-5}$M.

In an exemplified embodiment comprising a SAMI-$CO_2$ sensor, the sulfonephthalein, bromothymol blue (BTB) is the analyte-selective reagent or indicator solution. The two wavelengths of BTB are 434 nm for the acid, or protonated HL form, and 620 nm for the base, or unprotonated $L^{2-}$ form (FIG. 3). The sensor response could be based on the individual absorbances at either 434 or 620 Nm but by combining the absorbances in a ratio, i.e. $A_{620}/A434$. The sensor response $A_R$ is therefore calculated by combining the absorbances at two different wavelengths of the indicator solution in a ratio, i.e. $A_R=A_{\lambda,1}/A_{\lambda,2}$. The response as shown herein is independent of cell pathlength and total indicator concentration, two potential sources of variability and drift.

The sensor response is calculated using an equation that relates the absorbance ratio directly to the indicator solution pH. In an exemplified embodiment using a SAMI-$CO_2$ sensor with BTB indicator, the absorbance ratio is $A_{620}/A_{434}$. The solution pH at infinite dilution (activity coefficients=1) can be described using a combination of the indicator equilibrium expression with Beer's law [10,11], $$pH = pK_a + \frac{\log[L^{2-}]}{[HL^-]} \quad (2)$$

with $$\frac{[L^{2-}]}{[HL^-]} = \frac{A_R - \varepsilon_{620a}/\varepsilon_{434a}}{\varepsilon_{620b}/\varepsilon_{434a} - A_R\varepsilon_{434b}/\varepsilon_{434a}} \quad (3)$$

where $A_R = A_{620}/A_{434}$ and the subscripted $\varepsilon$'s represented the molar absorptivities for BTB with "a", the acid form of the indicator, and "b" the base form of the indicator. As shown in FIG. 3, the absorbance spectra for the acid and base forms overlap and both indicator forms contribute to the absorbances at the analytical wavelengths. These overlapping absorbances are accounted for in the derivation of Equation 3.

The SAMI response, $R_{CO2}$, is calculated from Equations 2 and 3:

$$R_{CO2} = -\log\left(\frac{A_R - \varepsilon_{620a}/\varepsilon_{434a}}{\varepsilon_{620b}/\varepsilon_{434a} - A_R\varepsilon_{434b}/\varepsilon_{434a}}\right) = +pK_a - pH. \quad (4)$$

From this equation, it is apparent that the sensor response is a fundamental property of the analyte-selective reagent chemistry. The response therefore has a physical meaning, representing the indicator solution pH offset from the pKa. Equation 4 also shows that the response $R_{CO2}$ is only dependent upon the molar absorptivities and absorbance ratio. In turn, the absorbance ratio $A_R$ is dependent upon the original solution alkalinity, ambient $pCO_2$ and temperature. Thus, every SAMI and likewise every reagent-based optical chemical sensor/analyzer whose reaction results in two light absorbing forms run under the calibration-free conditions of the subject invention will have an identical response for an identical indicator solution assuming good wavelength and absorbance accuracy.

The calibration-free system of the subject invention requires careful solution preparation, wavelength calibration and stray light rejection. The following provides specific examples of means by which these parameters were controlled for the calibration-free system described in the exemplified embodiment. Similar choices in detector size, photodiode type, solution preparation, handling and storage would be apparent to those skilled in the art in designing other calibration-free systems.

Good absorbance, i.e. photometric accuracy, is achieved by careful design and evaluation of the optical system. Detector size should be selected to increase the signal-to-noise (S/N) ratio without significantly compromising linearity due to inadequate resolution. For example, the SAMI uses a miniature f/2.5 spectrograph with 10 nm mm$^{-1}$ reciprocal linear dispersion (Model MS10, American Holographic, Littleton, Mass.) and three photodiode detectors (G1962 and S2386-5K, Hamamatsu Corp., Bridgewater, N.J.). Detectors are positioned with the center wavelength at 434, 620, and 740 nm in the spectrograph focal plane. Detector photosensitive surface areas are 2.3, 2.4 and 2.4 mm$^2$ at 434, 620, and 740 nm, respectively, resulting in a resolution of ~23–24 nm. The S/N at 434, 620 and 740 is typically ~2500, 4500, and 4500, respectively.

In an exemplified embodiment, a SAMI-CO$_2$ sensor comprises three detectors, two standard silicon detectors and one GaP photodiode in a diffraction grating based system. Other detector arrangements including interference filter based light separation systems and scanning wavelength instruments also are suitable for use in the subject calibration-free system. Likewise, detectors can be arranged in a photodiode array within the reagent-based optical chemical sensors/analyzers. It is only necessary that these systems provide photometric accuracy.

Photometric accuracy in spectrophotometric measurements can be limited by stray light. Tungsten light sources emit considerably more light in the near-infrared (NIR) than in the visible spectrum and measurements at short wavelengths, such as 434 nm, are especially susceptible to stray NIR light. Stray light levels, evaluated with a 600 nm long pass filter, were found to be as high as 20% at 434 nm in an exemplified embodiment. A heat-absorbing filter (005GF13-25, Andover Corp., Salem, N.H.) placed at the spectrograph filter optic input reduced stray light to 0.1%. This filter however significantly reduced the S/N at 740 nm. In a specific embodiment, a GaP photodiode (G1962, Hamamatsu) that is insensitive to NIR light was used in place of the broad-response Si photodiode at 434 nm. The GaP photodiode reduced stray light to less than 0.04% at 434 nm while maintaining a S/N of over 2500. As an additional check on absorbance accuracy each spectrograph was routinely evaluated with neutral density filters. Absorbances typically agree with the filters to within +/−0.003 a.u. based on these evaluations, which was within the reproducibility of the neutral density filter measurements.

Spectrograph absorbance accuracy also depends upon accurate wavelength calibrations. Thus, it is preferred that each 620 nm detector output is optimized in the lab with a 620+/−2 nm bandpass filter. The other detectors should be positioned to correspond to 434 and 740 nm relative to the 620 nm detector, based on the grating dispersion. The broad absorbance bands (FIG. 3) and detector bandpass relax the need for wavelength accuracy better than 2–3 nm.

The analyte-selective reagent, sensing solution, or indicator solution of the sensors of the subject invention should be reproducibly prepared. In the exemplified embodiment, a solution of 50 μM MBTB with 42 μeq l$^{-1}$ of NaOH was used as the sensing solution. The base was added to optimize the indicator pH response range[9]. The BTB and standardized NaOH were added to 1.00 kg deionized, degassed H$_2$O and the indicator solution was placed in polyethylene-coated aluminum bags. The indicator solution composition was checked by equilibrating it with a known pCO$_2$ and measurement of R$_{CO2}$ on a UV/VIS spectrophotometer.

The exemplified embodiment describes a SAMI-CO$_2$ response which is both reproducible between instruments and very stable the two conditions necessary for calibration-free performance. Although this embodiment departs from the conventional single-ended optrode design, similar performance can be expected for optrodes if the optrode is configured as in conventional colorimetric measurements, i.e. where the reagent is renewed and true solution absorbances are determined. Non-renewable ROCS have no means for determining I$_0$ and can therefore not take advantage of the improved performance offered by this approach. However, most fixed reagent sensor designs can be readily modified to accomodate the pump, valve and additional tubing. A wide variety of pumping mechanisms and valves are now available [15, 16] and they have proven to be very reliable for long-term measurements in harsh environments.

Many of the ROCS described have a membrane which traps the indicator solution. The ROCS need not contain such a membrane but sensors and analyzers in which the reagent is mixed directly with the analyte are also suitable for use in the subject calibration-free system.

The ratio techniques employed by the system of the subject invention, eliminates dependence on the system's operational parameters such as pathlength, light intensity, and the detector response function. Multi-wavelength detection and use of absorbance ratios take advantage of the two forms of a calorimetric reagent. Many calorimetric ROCS sensors utilize reagents of this type including those, for example, for pH, gases, metal ions, anions, organics, and biochemical compounds[17, 18, 19, 20].

Calibration-free operation is also facilitated if the sensor response is based on an equilibrium between the reagent solution and external sample. The sensor response becomes diffusion-independent in this case and is insensitive to changes in the diffusional boundary layer around the sensor membrane. This simplification also makes it possible to model the response based solely upon thermodynamic considerations. If the thermodynamic constants are available, such models are usefuil for evaluating the sensor response and detecting systematic measurement errors[21].

The calibration-free system of the subject invention can also be used with ROCs based on flourescent reagents. The fundamental response of these ROCS depends on the fluorophore quantum efficiency and concentration. As in any intensity-based measurement, the signal output reflects the detector response, light source output and additional instrumental parameters[22]. A fluorescence ratio of two forms of the fluorophore can be used[23]. Since the two forms are detected at different wavelengths however the ratio would not correct for wavelength dependent throughout and detector response. This would present an obstacle to designing sensors with an identical response. If the fluorophore did not exist in two forms, as found in quenching based $O_2$[24, 25, 26], the ratio approach could only be used if an additional $O_2$ insensitive fluorophore was included in the sensing solution.

Other absorbance-based sensors, such as optrodes, can be designed and operated in a similar fashion, making calibration-free optical chemical sensors available for a wide range ofbiomedical, industrial and environmental applications. Additionally, calibration-free ROCs can also be developed based on other approaches. Fluorescence lifetime-based ROCS are one example of a promising alternative[27]. Furthermore, the performance of non-renewable ROCS continues to be improved through innovative fabrication techniques[24, 26].

The subject calibration-free sensors still require initial characterization ofthe response. After the response is thoroughly evaluated and well-established, a single set of regression coefficients can be used to calculate analyte concentration from any one of the identically-designed sensors. Calibration-free sensors undoubtedly will require occasional checks on the instrument response. A single calibration standard could be used to determine if the instrument response matches the expected response and, if they do not agree, further evaluation of the instrument optical system or indicator chemistry may be necessary.

The following examples are offered to further illustrate but not limit both the compositions and the method of the present invention. All percentages are by weight and all solvent mixture proportions are by volume unless otherwise noted.

EXAMPLE 1

Determination of the Sensor to Sensor Reproducibility

The following results demonstrate that all sensors operated, as described above, have an identical response. The SAMI response ($R_{CO2}$) was determined in a water-filled thermostated chamber. Variable gas concentrations were obtained by mixing a 1600 ppm $CO_2$ standard with $CO_2$-free air using two mass flow controllers[9]. The chamber headspace was continuously monitored by a nondispersive infrared $CO_2$ analyzer (NDIR) (Model LI-6251, LiCOR, Inc., Lincoln, Nebr.) calibrated with N.I.S.T. traceable $CO_2$ gas standards (Air Liquide, Long Beach, Calif.). A circulating water pump mixed the equilibrator contents to insure complete equilibration. Equilibration temperature and barometric pressure were also monitored and used in the NDIR analyzer mole fraction ($XCO_2$) calculations[1,9]. The NDIR $pCO_2$ was calculated using, $$pCO_2 = X_{CO2(Wet)} P \qquad (5)$$

where $X_{CO2(Wet)}$ was the $CO_2$ mole fraction in water-saturated air determined by the NDIR and P was the barometric pressure.

Figure 4:
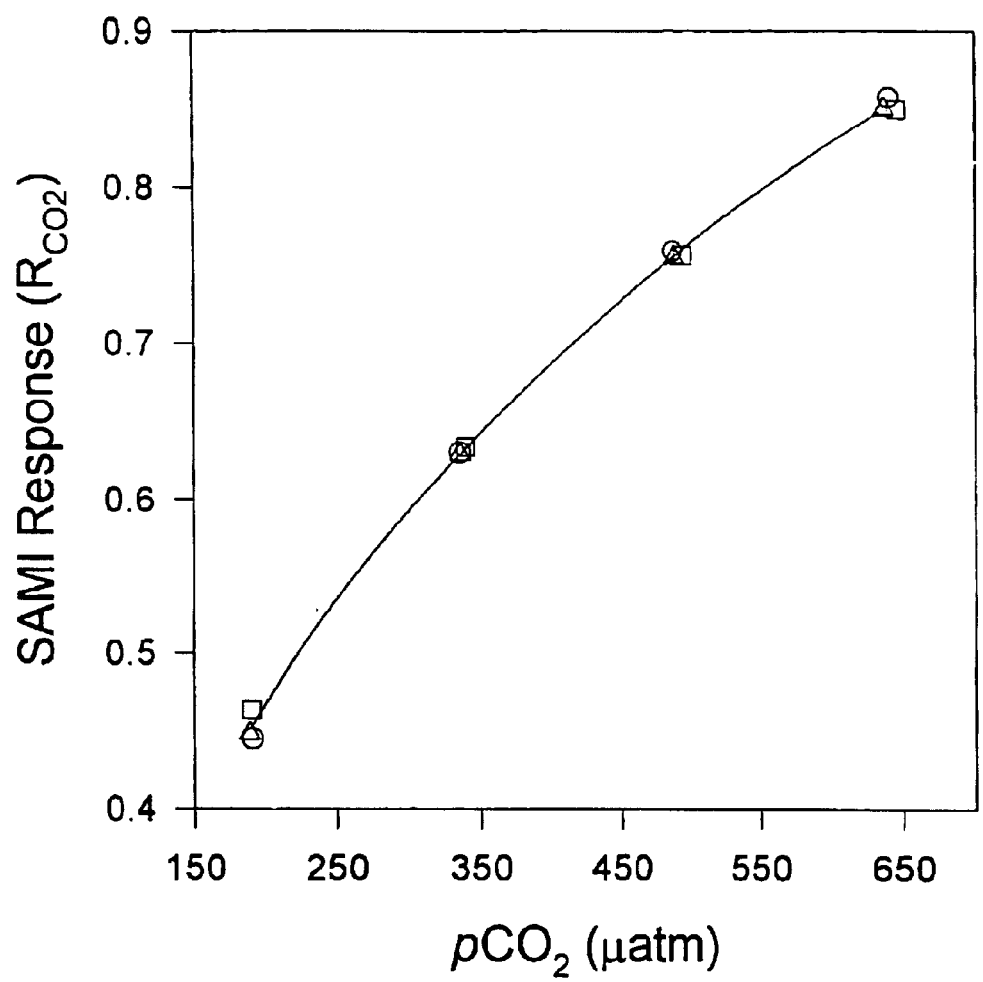
FIG. 4 shows the response of three different SAMI-$CO_2$ obtained over ~1 week period in October 1997 (O-SAMI 5, □-SAMI 6, Δ-SAMI 7). The solid curve represents the best fit to the average of the three SAMI responses at each $pCO_2$. Curves were fit to the equation $R_{CO2}=a(\log pCO_2)^2+b(\log pCO_2)+c$. Coefficients from the individual curve fits are given in Table 1 and comparisons of $pCO_2$ s are calculated from the different SAMI curves are shown in Table 2.

Three identically-designed SAMIs were compared. Prior to determining the response curves, each SAMI was carefully tested for wavelength and photometric accuracy and the same indicator solution was loaded into the reagent bags for each instrument. The 3 SAMI responses were then sequentially determined as described in Example 1. These results, presented in FIG. 4, show a nearly identical response between the different instruments. The $R_{CO2}$ from the 3 SAMIs at 20.5° C. range from 0.45 to 0.85, or a pH of ~0.40 (Equation 4), from 200–650 µatm $pCO_2$. Coefficients from curve fitting are shown in Table 1 and the $pCO_2$s calculated for different $R_{CO2}$s using these equations are shown in Table 2.

TABLE 1

Figure 8:
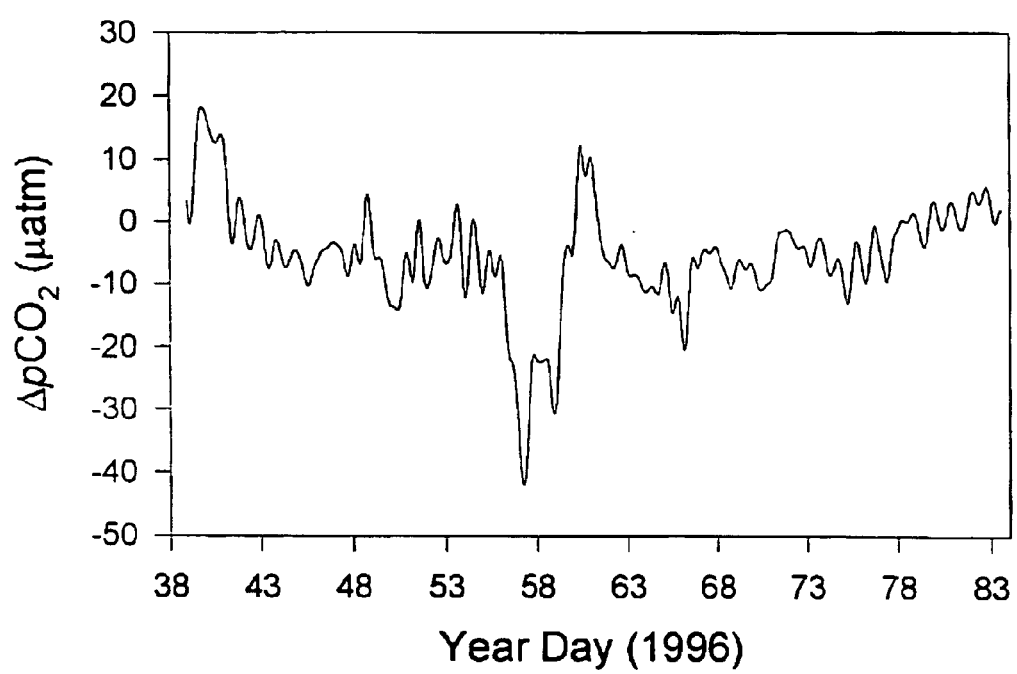
FIG. 8 shows the difference in $pCO_2$ determined at a single location but at two different depths on an ocean mooring off Cape Hatteras, N.C. The data were first low pass filtered to improve the figure clarity (reduced short-term variability). The ΔpCO is equal to SAMI 5 (10 m)-SAMI 6 (22 m). The difference is calculated over the period when both instruments were operational (SAMI 5 stopped functioning near year day 50 due to an electronic problem).

| | Curve fitting parameters for SAMI response date in FIGS. 4 and 8. | | | | |
| --- | --- | --- | --- | --- | --- |
| Coefficients | SAMI 5 Oct. 29, 1997 | SAMI 6 Oct. 21, 1997 | SAMI 7 Oct. 23, 1997 | Theoretical Curve | SAMI 5 Jan. 11, 1998 |
| a | 0.1076 | 0.1913 | 0.1437 | 0.1369 | 0.1087 |
| b | 0.2391 | −0.2444 | 0.0317 | 0.0655 | 0.2539 |
| c | −0.6606 | 0.0264 | −0.3682 | −0.4798 | −0.7015 |

Coefficients from a curve fit of the form: $R_{CO_2} = a(\log pCO_2)^2 + b(\log pCO_2) + c$

TABLE 2

Calculated $pCO_2$s (µatm) for different $R_{CO_2}$s using the equations in Table 1.

| $R_{CO_2}$ | SAMI 5 Oct. 29, 1997 | SAMI 6 Oct. 21, 1997 | SAMI 7 Oct. 23, 1997 | SAMI 5 Jan. 11, 1998 | Std.Dev.* |
|---|---|---|---|---|---|
| 0.40 | 166 | 150 | 160 | 167 | 8.1 |
| 0.45 | 194 | 181 | 190 | 195 | 6.7 |
| 0.50 | 227 | 217 | 224 | 227 | 5.1 |
| 0.55 | 264 | 258 | 263 | 263 | 3.2 |
| 0.60 | 307 | 305 | 307 | 305 | 1.2 |
| 0.65 | 356 | 358 | 358 | 352 | 1.2 |
| 0.70 | 412 | 418 | 415 | 405 | 3.0 |
| 0.75 | 475 | 485 | 480 | 466 | 5.0 |
| 0.80 | 546 | 561 | 553 | 534 | 7.5 |
| 0.85 | 627 | 645 | 636 | 612 | 9.0 |

*This is the standard deviation of the calculated $pCO_2$ for SAMI 5, SAMI 6, and SAMI 7.

The estimated $pCO_2$s from the three response curves agreed to within the uncertainty of the calibration procedure (1.8 µatm ave. standard deviation for the data in Table 2) in the range from 300–400 µatm which is the most common range encountered in marine studies.

Figure 5:
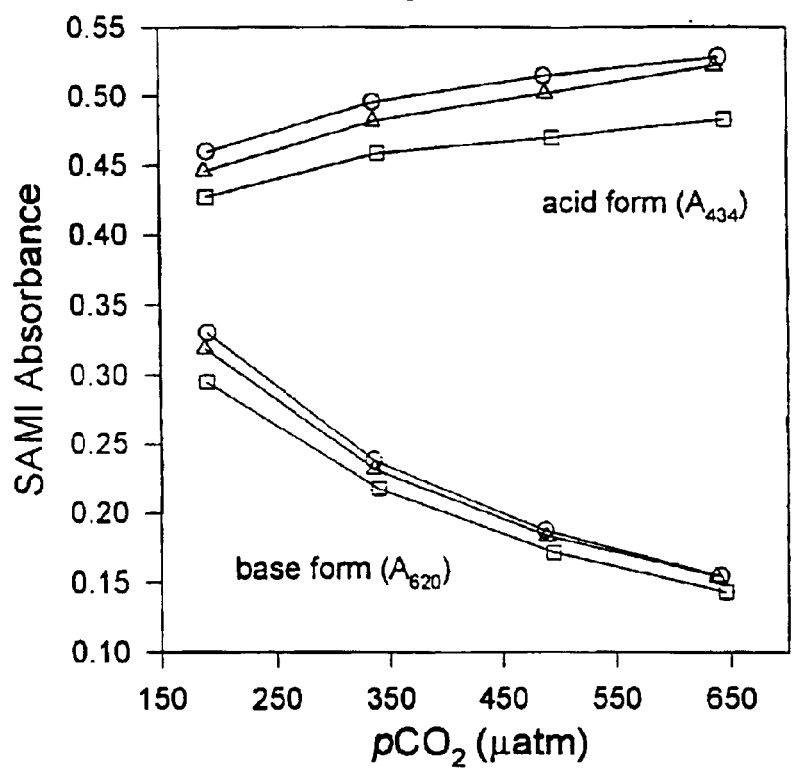
FIG. 5 shows SAMI absorbances (top) and absorbances ratio $A_R$ (bottom) used to calculated $R_{CO2}$ in Figure (O-SAMI 5, □-SAMI 6, Δ-SAMI 7).

The absorbance data used to generate FIG. 4 illustrate the importance of using absorbance ratios (FIG. 5). The absorbances differ between SAMIs by as much as 005 a.u. The consistently high and low absorbances between SAMIs suggested that the differences originate from optical pathlength differences, with SAMI 5 having the longest and SAMI 6 the shortest pathlength. The pathlength of the fiber optic cell (FIG. 2) is 0.75 cm but the pathlength can vary between SAMIs due to imprecise positioning of the fibers in the sealed fittings. Clearly, sensors that are based on absolute absorbances must have very carefully controlled pathlengths to achieve reproducible sensor-to-sensor performance. As indicated by the convergence of the response curves in FIGS. 4 and 5, the SAMI response ($R_{CO_2}$) is insensitive to pathlength variability.

Figure 6:
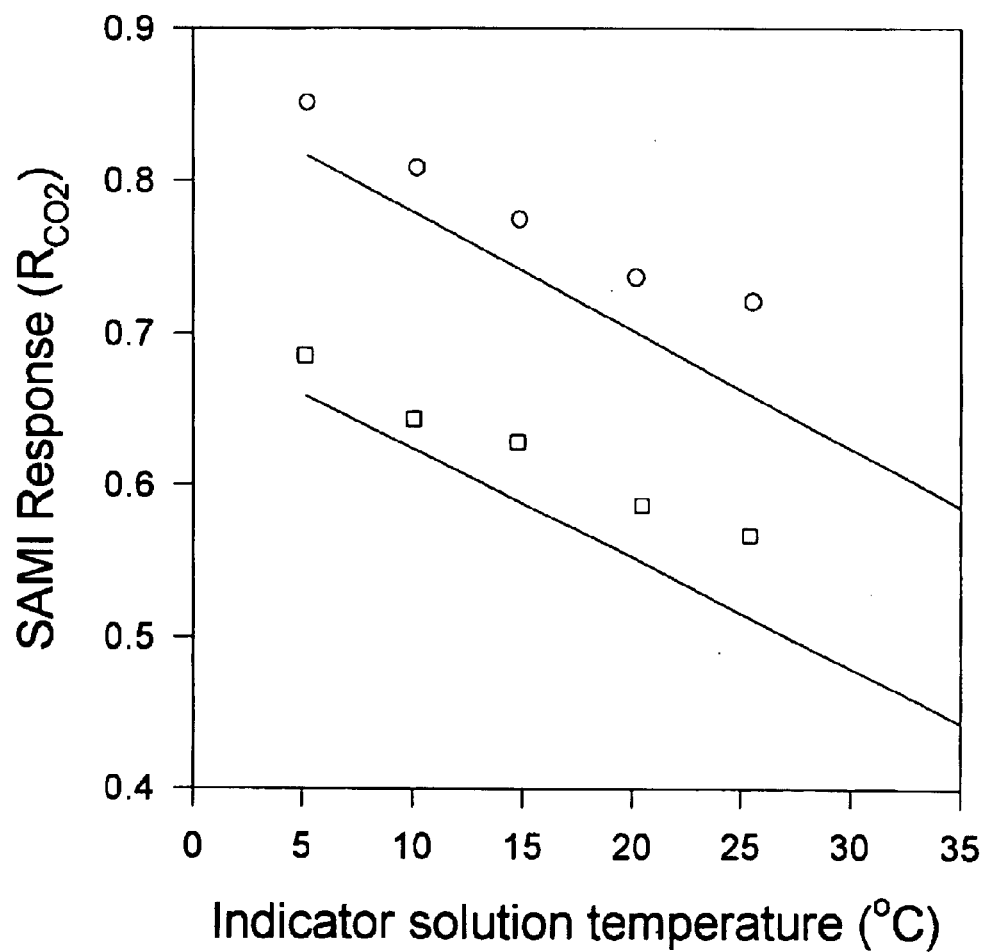
FIG. 6 shows the experimental and theoretical temperature response at 325 (□) and 506 μatm (O). The theoretical curves (solid lines) at 325 and 506 μatm have slopes of 0.0071 and 0.0076 $R_{CO2}$ units $°C^{-1}$, respectively. The experimental data curves (not shown) at 325 μatm and 506 μatm have slopes of 0.0058 and 0.0065 $R_{CO2}$ units $°C^{-1}$, respectively.

Most chemical sensors have a temperature dependent response and it is important to accurately quantify this dependence and correct for it in the recorded signal. The SAMI temperature response was evaluated by determining both the experimental and theoretical $R_{CO_2}$ at different temperatures and $pCO_2$s (FIG. 6). The sensor temperature dependence originates primarily from the temperature-dependent $CO_2$ solubility (a solution equilibrated with the same $pCO_2$ will have a different pH at different temperatures). $R_{CO_2}$ decreases as temperature increases as a result of this effect. The experimental temperature response followed the expected trend (FIG. 6) although the offset was present between the experimental and theoretical $R_{CO_2}$ as discussed above. The implications of FIG. 6 are that the temperature coefficient is significant and that the magnitude depends upon the $pCO_2$. During previous field deployments the SAMIs were calibrated as closely as possible to the expected seawater temperature to minimize the temperature correction.

EXAMPLE 2

Evaluation of Long-Term Stability

A reproducible sensor-to-sensor response as shown in FIG. 4 is one performance characteristic necessary for calibration-free operation. A second equally important quality is that the response must not change, or drift, over time.

Drift minimized in the SAMIs using three techniques: renewing the indicator reagent, periodic measurement of solution blanks, and use of absorbance ratios. Blanks are necessary not only to calculate absorbances but to also correct for wavelength-dependent intensity changes.

Figure 7:
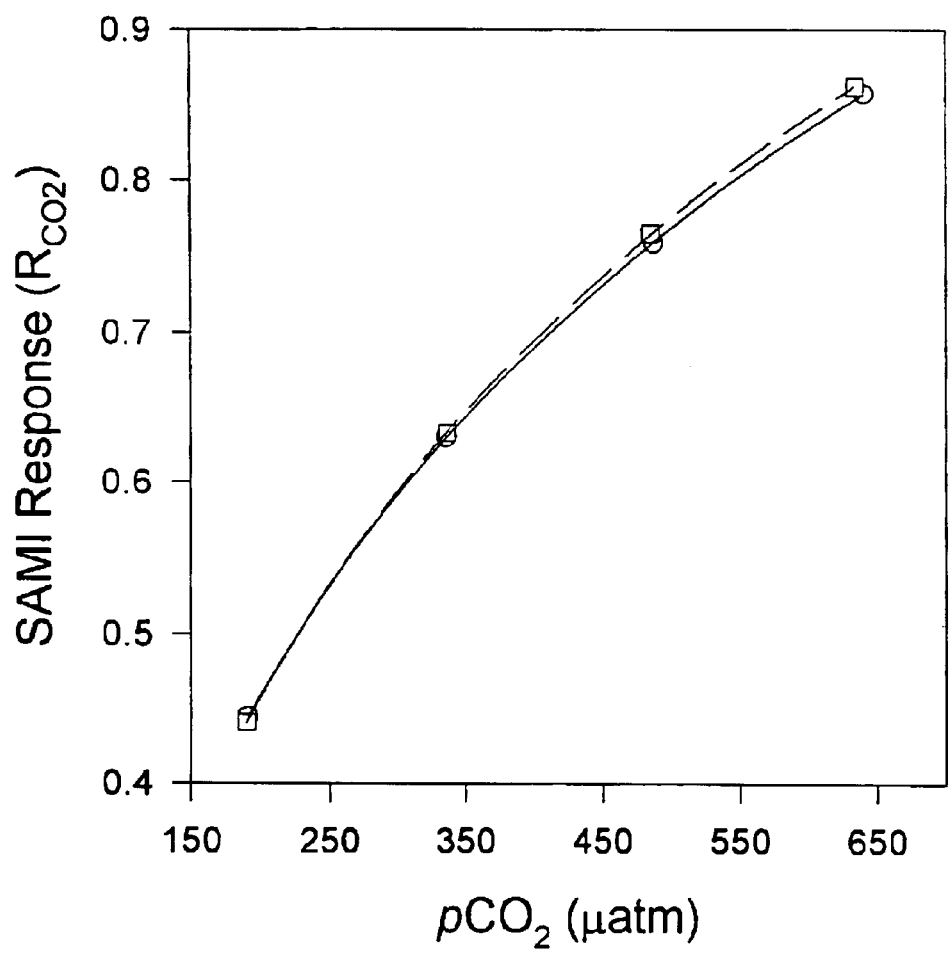
FIG. 7 shows the SAMI 5 response curves for data from Oct. 29, 1997 (FIG. 4) (O) and 74 days later on Jan. 11, 1998 (□). The Oct. 29, 1997 and Jan. 11, 1998 regression curves are shown as solid and dashed lines, respectively. Coefficients from the curves fits are given in Table 1.

Drift improvements by renewing the reagent, measuring blanks, and using absorbances ratios has not been systematically compared to the performance of ROCS that do not employ these techniques. However, an indirect comparison is provided from the literature where sparse long-term stability data have been reported for non-renewable intensity-based ROCS (see for example the recent SPIE volume *Chemical, Biochemical and Environmental Fiber Sensors IX,* June 1997). This summary is based on the criteria that a rigorous evaluation of long-term stability consists of regular accuracy checks without recalibration for a period greater than 1 week. A more specific example is given by examination of ROCS $CO_2$ sensors developed for oceanographic applications[12,13,14]. Almost no long term data have been presented for these sensors, which are all based on fixed reagents. In contrast, the SAMIs have demonstrated excellent stability from the very early stages of development[8,9]. A month-long in situ seawater test found no detectable drift in the response[9] and recent laboratory studies have shown no significant change in the response with time (FIG. 7). Although the two curves in FIG. 8 are not identical, the difference in $pCO_2$ determined from the curve fit equations is very small over the typical oceanographic range (Table 2). Verification of accuracy during ocean mooring deployments had been more difficult due to infrequent visits by supporting research vessels and spatial variability between the ship and the mooring. However, two SAMIs that were deployed on an ocean mooring off Cape Hatteras during 1996 give an indication of the long-term stability in the field (FIG. 8). The two $pCO_2$ signals, which were calculated from the same $R_{CO_2}$-$pCO_2$ response curves, show no systematic deviation with time over the ~50 days when the two instruments were operational. The large periodic differences between the two instruments correspond to temperature differences between the instrument depths indicating the presence of density stratification and associated concentration gradients with depth (DeGrandpre, unpubl., 1998). The combined data sets in this case provide an evaluation of the long-term stability in the field.

It should be understood that the examples and embodiments described herein are for illustrative purposes only and that various modifications or changes in light thereof will be suggested to persons skilled in the art and are to be included within the spirit and purview of this application and the scope of the appended claims.

References

1 MacCraith, B. D.; McDonagh, C.; McEvoy, A. K.; Butler, T.; O'Keefe, G.; Murphy, V. J. *Sol-Gel Sci. Tech.* 1998, 8, 1053–1061.
2 Spichiger-Keller, U. E. *Chemical Sensors and Biosensors for Medical and Biological Applications*, Wiley-VCH: Weinheim, 1998.
3 Angel, S. M. *Spectroscopy* 1987, 2 38–50.
4 Berman, R. J.; Christian, G. D.; Burgess, L. W. *Anal. Chem.* 1990, 62, 2066–2071.
5 Inman, S. M.; Stromvall, E. J.; Lieberman, S. H. *Anal. Chem Acta* 1989, 217, 249–262.
6 Vurek, G. G.; Fuestel, P. J.; Severinghans, J. W. *Ann. Biomed. Eng.* 1983, 11, 499–510.
7 DeGrandpre, M. D. *Proc SPIE-Int. Soc. Opt. Eng.* 1991, 1587, 60–66.
8 DeGrandpre, M. D. Anal. Chem. 1993, 65, 331–337.
9 DeGranpre, M. D.; Hammar, T. R.; Smith, S. P.; Sayles, F. L. *Limnol. and Oceanog.* 1995, 40, 969–975.
10 Byrne, R. H.; Breland, J. A. *Deep-Sea Res.* 1989, 36, 803–810.
11 Clayton, T. D.; Byrne, R. H. *Deep-Sea Res.* 1993,40, 2115–2129.
12 Goyet, C. ; Walt, D. R.; Brewer, P. G. *Deep-Sea Res.* 1992, 39, 1015–1026.
13 Goswami, K. ; Kennedy, J. A.; Dandge, D. K.; Klainer, S. M.; Tokar, J. M. *Proc. SPIE-Int. Soc. Opt. Eng.* 1990, 1172, 225–232.
14 Lefevre, N.; Ciabrini, J. P.; Michard, G.; Brient, B.; DuChaffaut, M.; Merlivat, *L. Mar. Chem.* 1993, 42, 189–198.
15 Jannasch, H.; Johnson, K. S.; Sakamoto, C. M. *Anal. Chem.* 1994, 66, 3352–3361.
16 Weeks, D. A.; Johnson, K. S. *Anal. Chem.* 1996, 68, 2717–2719.
17 Peterson, J. L.; Goldstein, S. R.; Fitzgerald, R. V.; Buckhold, D. K. *Anal. Chem.* 1980, 52, 864–869.
18 Zhou, Q.; Kritz, D.; Bonnell, L.; Sigel, G. *App. Opt.* 1989, 28, 2022–2025.
19 Chau, L. K.; Porter, M. D. *Anal. Chem.* 1990, 62, 1964–1971.
20 Radloff,D.; Matern, C.; Plaschke, M.; Simon, D.; Reichert, J.; Ache, H. J. *Sens. Actuators B* 1996, 35–36, 207–211.
21 DeGrandpre, M. D., Anal. Chem. 1999, 71, 1152–1159.
22 Ingle, J. D.; Crouch, S. R. *Spectrochemical Analysis.* Prentice-Hall: New Jersey, 1988.
23 Thompson, R. B.; Jones, E. R. *Anal. Chem.* 1993, 65, 730–734.
24 McDonagh, C.; MacCraith, B. D.; McEvoy, A. K. *Anal. Chem.* 1998, 70, 45–50.
25 Wolfbeis, O. S.; Posch, H. E.; Kroneis, H. W. *Anal. Chem.* 1985, 57, 2556–2561.
26 Klimant, I.; Meyer, V.; Kuhl, M. *Linmol Oceanog.* 1995, 40, 1159–1165.
27 Draxler, S.; Lippitsch, M. E. *Proc. SPIE-Int. Soc. Opt. Eng.* 1993, 2085, 61–67.

What is claimed is:

1. A method of operating absorbance-based chemical sensors to achieve calibration-free measurements, the method comprising the steps of:

a) establishing wavelength accuracy to within about 2–3 nanometers;

b) eliminating stray light at all wavelengths to about less than 0.1% incident light;

c) preparing an analyte-selective reagent at a concentration;

d) equilibrating the analyte-selective reagent to an analyte;

e) taking an intensity reading of the equilibrated analyte-selective reagent and analyte at a first wavelength ($I_{\lambda 1}$) with a reagent-based optical chemical sensor, wherein the sensor has been modified to allow the renewal of an analyte-selective reagent, wherein the first wavelength corresponds to an un-reacted form of the analyte-selective reagent, and taking an intensity reading of the equilibrated analyte-selective reagent and analyte at a second wavelength ($I_{\lambda 2}$), wherein the second wavelength corresponds to a reacted form of the analyte-selective reagent;

f) replacing the equilibrated analyte-selective reagent and analyte with a spectrophotometric blank solution;

g) taking an intensity reading of the blank solution at the first wavelength ($I_{\lambda 10}$) and taking an intensity reading of the blank solution at the second wavelength ($I_{\lambda 20}$);

h) calculating an absorbance ratio using the equation $A_R = A_{\lambda 1}/A_{\lambda 2}$, where $A_R$ is the absorbance ratio, $A_{\lambda 1}$ is absorbence at the first wavelength and $A_{\lambda 2}$ is absorbance at the second wavelength and, wherein $A_{\lambda 1}$ and $A_{\lambda 2}$ are determined by $$A_\lambda = -\log(I_\lambda/I_{\lambda 0}); \quad \text{and}$$

i) calculating the sensor response with the molar absorptivities ($\epsilon$) of the reacted (a) form of the analyto-selective reagent and the un-reacted form (b) of the analyte-selective reagent using the equation $$R = -\log\left(\frac{A_R - \epsilon_{\lambda 1a}/\epsilon_{\lambda 2a}}{\epsilon_{\lambda 1b}/\epsilon_{\lambda 2a} - A_R \epsilon_{\lambda 2\beta}/\epsilon_{2a}}\right) = +pK_a - pH,$$

wherein when the analyte-selective reagent is prepared accurately and reproducibly at the concentration sensor readings between sensors are calibration-free.

2. The method of claim 1, wherein said first wavelength is 620 nanometers and said second wavelength is 434 nanometers.

3. The method of claim, wherein said analyte-selective reagent is colorimetric.

4. The method of claim 1, wherein said reagent is renewed by a pump and at least one valve.

5. The method of claim 4, wherein said pump and at least one valve are selected from the group consisting of at least one peristaltic pump, at least one syringe pump, at least one positive displacement pump, at least one solenoid pump and valve and at least one pinch valve.

6. The method of claim 1, wherein said reagent is renewed by a solenoid pump and valve.

7. The method of claim 1, wherein said reagent-based optical chemical sensor is a Submersible Autonomous Moored Instruments for $CO_2$.

8. The method of claim 7, wherein said analyte-selective reagent is bromothymol blue.

* * * * *